United States Patent [19]

Yamanaka et al.

[11] Patent Number: 4,803,276

[45] Date of Patent: Feb. 7, 1989

[54] 1-(IMIDAZO[1,2-A]PYRIDIN-6-YL)-2-ALKANONE DERIVATIVES AND (IMIDAZO[1,2-A]PYRIDIN-6-YL) ACETALDEHYDE DERIVATIVES

[75] Inventors: Motosuke Yamanaka, Chiba; Kazutoshi Miyake, Ibaraki; Shinji Suda, Ibaraki; Hideto Ohhara, Ibaraki; Toshiaki Ogawa, Ibaraki, all of Japan

[73] Assignee: Eisai Co., Ltd., Tokyo, Japan

[21] Appl. No.: 107,473

[22] Filed: Oct. 9, 1987

Related U.S. Application Data

[62] Division of Ser. No. 844,013, Mar. 26, 1986, Pat. No. 4,751,227.

[30] Foreign Application Priority Data

Mar. 26, 1985 [JP]  Japan .................................. 60-59450

[51] Int. Cl.$^4$ ............................. C07D 471/04
[52] U.S. Cl. .................................... 546/121
[58] Field of Search ........................ 546/121

[56] References Cited

FOREIGN PATENT DOCUMENTS 3406329  8/1985  Fed. Rep. of Germany .

Primary Examiner—Mary C. Lee
Assistant Examiner—Bernard I. Dentz
Attorney, Agent, or Firm—Wenderoth, Lind & Ponack

[57] ABSTRACT

Novel 1-(imidazo[1,2-a]pyridin-6-yl)-2-alkanone derivatives and (imidazo [1,2-a]pyridin-6-yl) acetaldehyde derivatives are provided. The novel derivatives are intermediates for the production of 5-(6-imidazo[1,2-a]pyridyl)pyridine derivatives which are useful as cardiotonics.

1 Claim, No Drawings

1-(IMIDAZO[1,2-A]PYRIDIN-6-YL)-2-ALKANONE DERIVATIVES AND (IMIDAZO[1,2-A]PYRIDIN-6-YL) ACETALDEHYDE DERIVATIVES

This application is a division of application Ser. No. 844,013 filed Mar. 26, 1986 now U.S. Pat. No. 4,751,227.

FIELD OF THE INVENTION

The present invention relates to novel 5-(6-imidazo[1,2-a]pyridyl)pyridine derivatives possessing excellent cardiotonic effect. More particularly, the present invention relates to novel 5-(6-imidazo[1,2-a]pyridyl)pyridine derivatives and pharmacologically acceptable salts thereof and a process for producing the same as well as pharmaceutical compositions comprising the same.

BACKGROUND OF THE INVENTION

A serious cause for congestive heart failures is depressing in contraction of heart muscle. For treating such heart failures, digitalis preparations have been used heretofor. The digitalis preparations have already had a history for 200 years and have become almost a synonym for cardiotonics. However, the digitalis preparations are accompanied by the serious problems that a toxic-to-therapeutic ratio is narrow and therapeutic effect is also insufficient.

Cardiotonics acting on sympathetic nerves such as isoprotenol, dopamine, dobutamine, etc. have also been widely used. However, these cardiotonics not only have side effects such as increase in heart rate, arrythmogenicity, etc., but also exhibit their effect only by an intravenous administration. Accordingly, these cardiotonics cannot be used for treating chronic congestive heart failures.

Thus, attention has now been focused on development of cardiotonics which are effective by oral administration and have a broad therapeutic range and an appropriately long duration of action, and such cardiotonics have been earnestly desired.

The present inventors have investigated compounds having a potent and long acting cardiotonic action by oral administration over long periods of time and finaly found that the following compounds can achieve the desired purpose and have thus accomplished the present invention.

SUMMARY OF THE INVENTION

The present invention is concerned with novel imidazo[1,2-a]pyridinylpyridine derivatives represented by general formula (I):

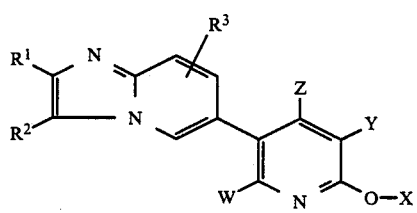
(I)

wherein X represents hydrogen atom or methyl group; Y represents cyano group, carboxamido group, hydrogen atom, amino group or a halogen atom; Z represents hydrogen atom or a lower alkyl goup; W represents hydrogen atom or a lower alkyl group; $R^1$ represents hydrogen atom, a lower alkyl group, phenyl group, a group shown by formula: —$CH_2R^4$ in which $R^4$ is a lower alkoxy group, or a group shown by formula:

in which $R^5$ and $R^6$ are hydrogen atom or a lower alkyl group; $R^2$ represents hydrogen atom or a halogen atom; and $R^3$ represents hydrogen atom, a lower alkyl group or a halogen atom; and a pharmacologically acceptable salt thereof, and a process for producing the same as well as medical compositions containing the same.

DETAILED DESCRIPTION OF THE PREFERRED EMBODIMENTS

The compounds of the present invention are novel compounds represented by general formula (I):

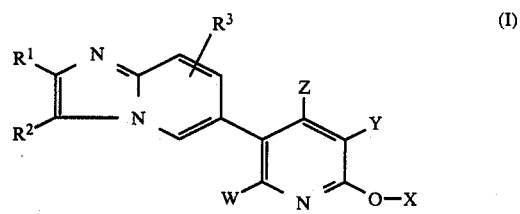
(I)

wherein X represents hydrogen atom or methyl group; Y represents cyano group, carboxamido group, hydrogen atom, amino group or a halogen atom; Z represents hydrogen atom or a lower alkyl group; W represents hydrogen atom or a lower alkyl group; $R^1$ represents hydrogen atom, a lower alkyl group, phenyl group, a group shown by formula: —$CH_2R^4$ in which $R^4$ is a lower alkoxy group, or a group shown by formula:

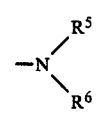

in which $R^5$ and $R^6$ are hydrogen atom or a lower alkyl group; $R^2$ represents hydrogen atom or a halogen atom; and $R^3$ represents hydrogen atom, a lower alkyl group or a halogen atom, that are not described in publications, and pharmacologically acceptable salts thereof; and a process for producing the same as well as medical compositions containing the same.

In the compound (I) of the present invention, the lower alkyl group for Y, Z, W, $R^1$, $R^5$, $R^6$ and $R^3$ is a straight or branched alkyl group having 1 to 6 carbon atoms, for example, methyl, ethyl, n-propyl, isobutyl, 1-methylpropyl, tert-butyl, n-pentyl, 1-ethylpropyl, isoamyl, n-hexyl, etc. The lower alkoxy group for $R^4$ is a lower alkoxy group corresponding to the above-described lower alkyl group. Further the halogen atom for Y, $R^2$ and $R^3$ is specifically fluorine, chlorine, bromine or iodine.

In general formula (I), when X is hydrogen atom, tautomers represented by the following structural formula (II):

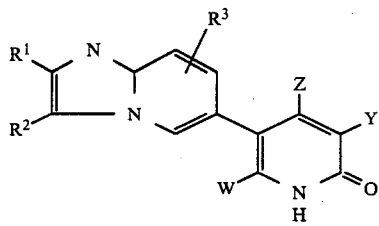

are involved; these tautomers are, needless to say, included within the scope of the present invention. The tautmers may also be co-present as an equilibrium mixture.

The pharmacologically acceptable salt of the compound of the present invention refers to a conventional non-toxic salt. Specific examples of such salts include alkali metal salts such as sodium salts, potassium salts, etc.; alkaline earth metal salts such as calcium salts, magnesium salts, etc.; ammonium salts; organic base salts such as trimethylamine salts, pyridine salts, picoline salts, dicyclohexylamine salts, N,N'-dibenzylethylenediamine salts, etc.; inorganic acid salts such as hydrochlorides, hydrobromides, sulfates, phosphates, etc.; organic acid salts such as formates, acetates, trifluoroacetates, maleates, tartarates, metahnesulfonates, benzenesulfonates, toluenesulfonates, etc.; salts with amino acids such as arginine salts, ornithine salts, etc.

In addition to the above-mentioned cardiotonic effect, the compounds of the present invention have characteristics that increase in heart rate is not significant, they have a vasodilator activity and an inhibitory effect of platelet-aggregation, and a safety margin is wide, and so forth.

Accordingly, an object of the present inventiion is to provide novel compounds having an excellent cardiotonic action.

A further object of the present invention is to provide novel compounds having a potent and long acting cardiotonic action by oral administration.

For producing the compounds of the present invention, there are many processes. Of these processes, representative exampls are shown below.

Preparation Process 1

In formula (I) wherein X is H and Y is CN:
The compound represented by the following general formula (III):

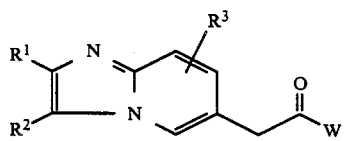

wherein $R^1$, $R^2$, $R^3$ and W have the same significances as described above, is reacted with the compound represented by the following general formula (IV):

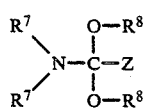

wherein Z has the same significance as described above; and $R^7$ and $R^8$ represent a lower alkyl group, to obtain the compound represented by the following general formula (V):

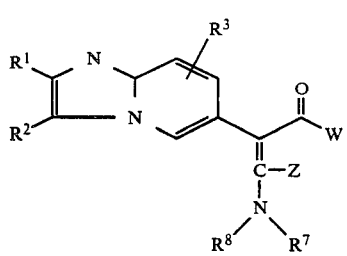

wherein $R^1$, $R^2$, $R^3$, $R^7$, $R^8$, W and Z have the same significances as described above (first step).

Then, the obtained compound (V) is reacted with α-cyanoacetamide under a basic condition to obtain the compound (II') represents by general formula (II'):

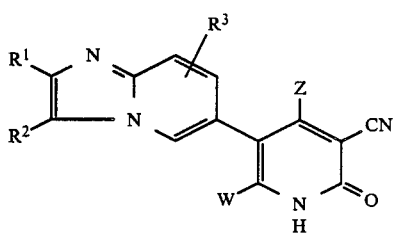

wherein $R^1$, $R^2$, $R^3$, W and Z have the same significances as described above (second step).

The reaction at the first step is conducted at room temperature to 120° C. in the presence of or absence of solvents in a conventional manner. Examples of the solvents include acetonitrile, dimethylformamide, tetrahydrofuran, dioxane, benzene, hexamethylphosphoramide, ether, etc. Where no solvent is used, the use of the compound (IV) in an excess amount gives preferred results.

The reaction at the second step can be carried out by heating in solvents in the presence of basic condesing agents. Specifically, preferred results are obtained by conducting the reaction in solvents such as Lower alcohols, e.g., methyl alcohol, ethyl alcohol, propyl alcohol, etc., dimethylformamide or hexamethylphosphormaide, etc. in the presence of bases such as alkali lower alkoxides, preferably sodium methoxide or sodium ethoxide. Specific examples of preferred combinations of other solvents and bases are the combination of tetrahydrofuran, acetonitrile, dioxane, etc. as the solvent and as the base, sodium hydride, lithium diethylamide, lithium isopropylamide, etc.

Preparation Process 2

In formula (I) wherein Y is carboxamido group or amino group, the compounds of the present invention can be produced, for example, by the following process.

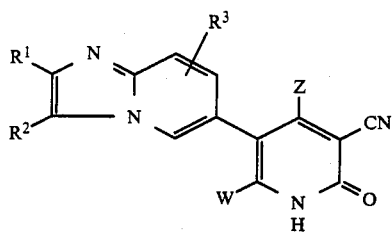 (II')

wherein $R^1$, $R^2$, $R^3$, Z and W have the same significances as described above.

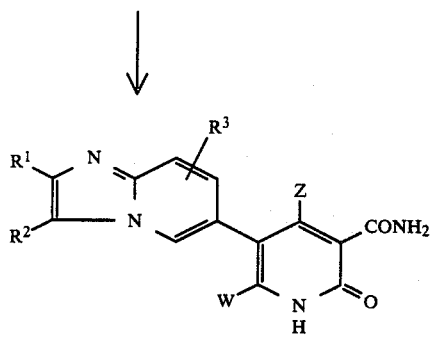 (II'')

↓ Hoffman Rearrangement

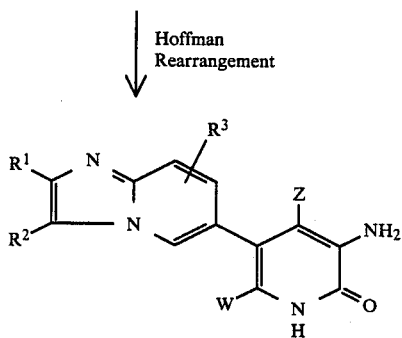 (II''')

Namely, the 1,2-dihydro-5-(imidazo[1,2-a]pyridin-6-yl)2-oxo-3-pyridinecarbonitrile derivative shown by general formula (II') is heated at 90° to 100° C. for 30 to 60 minutes in concentrated sulfuric acid to obtain the compound represented by general formula (II'') which is one of the products. The thus obtained compound (II'') is further reacted with a hypohalite under an alkaline condition to obtain the compound represented by general formula (II''') which is one of the products. As the hypohalite, hypobromite or hypochlorite is preferably used. The reaction temperature is at about 40° to about 100° C., preferably 70° to 100° C.

Preparation Process 3

Where Y is hydrogen atom in formula (I), the compound of the present invention can be produced, for example, by the following process.

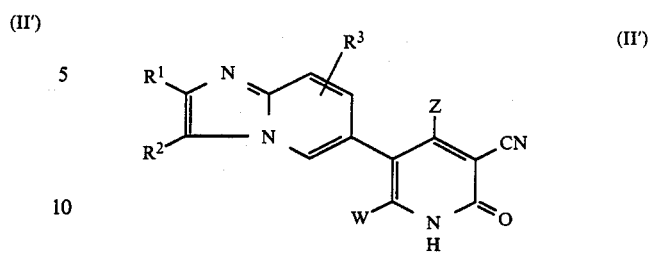 (II')

wherein $R^1$, $R^2$, $R^3$, W and Z have the same significances as described above.

↓

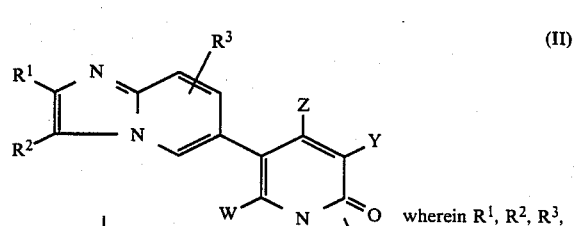 (II'''')

Namely, the 1,2-dihydro-5-(imidazo[1,2-a]pyridin-6-yl)-2-oxo-3-pyridinecarbonitrile derivative represented by general formula (II') is heated at 80° to 200° C. in aqueous solution of a mineral acid to obtain the compound (II'''') which is one of the products. As a preferred method, heating is conducted at 100° to 180° C. for about 15 to 30 hours in a 80% aqueous solution of phosphoric acid or in a 80% aqueous solution of sulfuric acid.

Preparation Process 4

Where X is $CH_3$ in formula (I), the compound can be produced, for example, by the following process:

(II)

wherein $R^1$, $R^2$, $R^3$, W, Z and Y have the same significances as described above.

↓

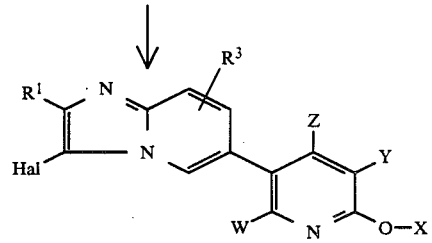

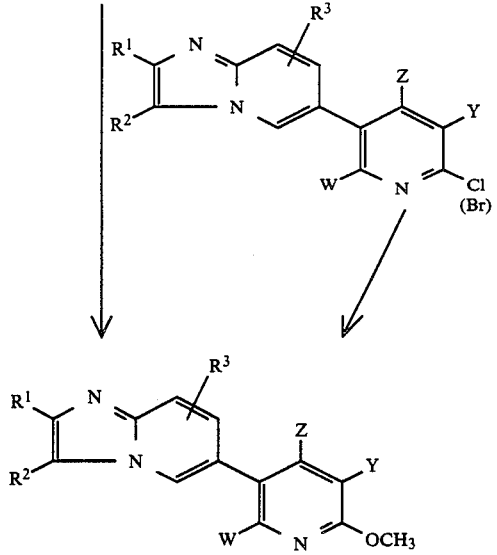

Namely, it is possible to prepare by any of the following processes.

(1) The compound represented by general formula (II) is heated together with phosphorous oxychloride or phosphorous oxybromide to obtain the chlorine or bromine product shown by general formula (VI). Then, the compound (VI) is heated together with alkali metal salts of methanol, preferably sodium methoxide, in the presence of alcohols, acetone, methylene chloride, chloroform, dioxane, tetrahydrofuran or N,N-dimethylformamide to obtain the compound (I') which is one of the products.

(2) The compound represented by geneeral formula (II) is treated with methyl halides such as methyl chloride, methyl bromide, etc. or dimethyl sulfide, in alcohols, acetone, methylene chloride, chloroform, dioxane, tetrahydrofuran, N,N -dimethylformamide in the presence of alkalis such as sodium carbonate, potassium carbonate, sodium methoxide, silver carbonate, etc. to obtain the compound (I') which is one of the products.

Preparation Process 5

Where $R^2$ is halogen in formula (I), the compound can also be prepared by the following process.

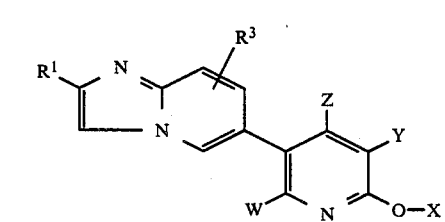

wherein $R^1$, $R^3$, X, Y, Z and W have the same significances as described above.

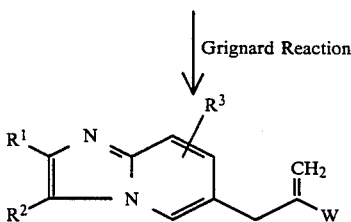

wherein Hal represents a halogen atom.

Namely, the compound represented by formula (I'') is reacted with chlorine or bromine at room temperature to 100° C. in solvents such as acetic acid, methylene chloride, chloroform, etc.; alternatively, the compound (I'') is reacted with N-chlorosuccinimide or N-bromosuccinimide at 40 to 100° C. in solvents such as N,N-dimethylformamide, dimethylsulfoxide, methylene chloride, chloroform, etc. to obtain (I''') which is one of the products.

Process for Producing Starting Material

In the process for producing the compounds of the present invention, the compound represented by general formula (III) which is used as the starting material can be prepared, for example, by the following processes.

(Preparation Process 1)

The process is illustratively shown below.

[First Step]

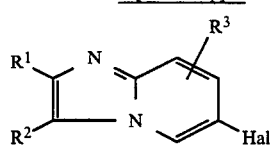

wherein Hal represents a halogen atom, $R^1$ has the same significance as described above, $R^3$ represents fluorone atom or a lower alkyl group; and $R^2$ represents hydrogen atom.

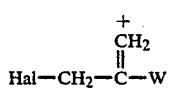

wherein Hal and W have the same significances as described above.

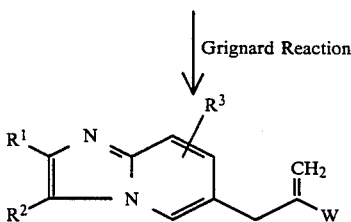

Grignard Reaction wherein $R^1$, $R^3$ and have the same significances as described above; and $R^2$ represents hydrogen atom.

[Second Step]

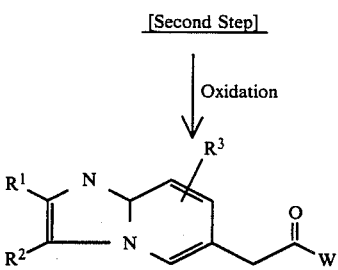

(III)

wherein $R^1$, $R^3$ and W have the same significances as described above, and $R^2$ represents hydrogen atom.

Preparation Process 1 is described below in more detail.

First Step

It i a step for preparing the compound represented by general formula (IX) by the reaction of the 6-halogenoimidazo[1,2-a]pyridine derivative shown by general formula (VII) and a β-alkylallyl shown by general formula (VIII). As in conventional Grignard reaction, the compound represented by general formula (VII) is first reacted with magnesium in solvents of ether type such as diethyl ether, tetrahydrofuran, dibutyl ether, diglime, etc. or in solvents of hydrocarbon type such as toluene, xylene, tetraline, etc. to form a Grignard reagent; then, the Grignard reagent is reacted with the β-alkylallyl halide (III). A preferred example is specifically shown below: the compound represented by general formula (VII) is added to 4 equivalents of magnesium in diethyl ether or tetrahydrofuran using 3 equivalents of ethyl bromide to form a Grignard reagent. Then, a solution of 4 equivalents of the β-alkylallyl halide in diethyl ether or tetrahydrofuran is reacted with the Grignard reagent to conduct the reaction. The reaction is carried out at room temperature to reflux temperature.

Second Step

It is a step of oxidizing the compound (IX) obtained at the first step to obtain the compound represented by general formula (III).

Representative examples of oxidation include a method for oxidation which comprises introducing ozone below 10° C. into compound (X) in a solvent such as diluted hydrochloric acid, methanol-water, methanol-diluted hydrochloric acid, acetic acid-water, methanol, acetic acid, methylene chloride, chloroform, etc., a method for oxidation which comprises treatment of compound (X) with osmium tetraoxide and periodate, osmium tetraoxide and hydrogen peroxide, etc. in a solvent such as dioxane, pyridine, tetrahydrofuran, alcohols, and so forth. One of the most preferred methods comprises introducing ozone at about 5° C. in methanol-diluted hydrochloric acid or acetic acid-water.

Preparation Process 2

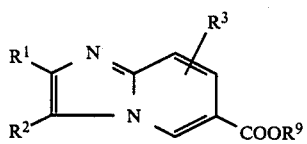

(X)

wherein $R^9$ is hydrogen or a lower alkyl group and, $R^1$, $R^2$ and $R^3$ have the same significances as described above.

[First Step]

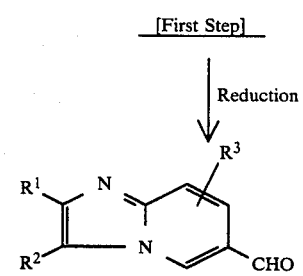

(XI)

+

$O_2NCH_2W$ (XII)

wherein W represents hydrogen atom or a lower alkyl group.

[Second Step]

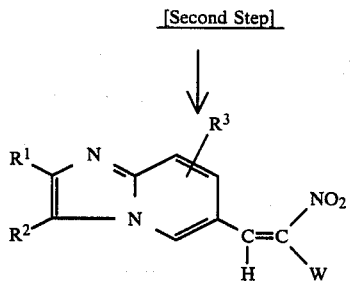

(XIII)

wherein W has the same significance as described above.

[Third Step]

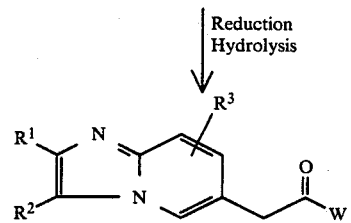

(III)

wherein $R^1$, $R^2$, $R^3$ and W have the same significances as described above.

Preparation Process 2 is described below in more detail.

First Step

It is a step of reducing the compound represented by general formula (X) which is a starting material prepared by a known process to prepare the formyl compound represented by general formula(XI). The reaction is carried out at reaction temperatures lower than −40° C. generally using as a reducing agent, lithium aluminum hydride, hydride, diisobutylamuminum hydride, etc. and as a solvent, diethyl ether, tetrahydrofuran, dioxane, toluene, dichloroethane, etc.

Second Step

It is a step of condensing the formyl compound represented by general formula (X) with a nitroalkane (XII) to obtain the compound represented by general formula (XIII).

The nitroalkane (XII) specifically means a nitro lower alkane such as nitromethane, nitroethane, nitropropane, nitrobutane, etc.

The condensation is carried out generally in the presence of, for example, alkyl amines, ammonium acetate, β-alanine, etc.

Third Step

In the reaction, the compound represented by general formula (XIII) is reduced and hydrolyzed to obtain the compound represented by general formula (III). The reaction is carried out in a conventional manner. Giving an example for providing preferred results, the compound (XIII) is treated with concentrated hydrochloric acid with heating, in a water-containing alcohol solvent in the presence of iron or ferrous chloride hydrate, or treated with zinc powders in acetic acid.

Among the formyl compounds represented by general formula (XI) used as the starting materials at the second step, the compounds wherein $R^2$ is hydrogen atom and $R^3$ is hydrogen atom, a lower alkyl group or fluorine atom can also be obtained by reacting the aforesaid compound (VII) with magnesium in solvents of ether type such as diethyl ether, tetrahydrofuran, dibutyl ether, diglime, etc. or in solvents of hydrocarbon atype such as toluene, xylene, tetraline, etc. to form Grignard reagents and then reacting the Grignard reagents with alkyl orthoformates, N,N-dimethylformamide or magnesium bromide formate. In the case of a preferred specific example, these compounds can be prepared by adding the compound (VII) to 4 equivalents of magnesium in a diethyl ether or tetrahydrofuran solvent, forming the Grignard reagent using 3 equivalents of ethyl bromide, and then reacting the Grignard reagent with 4 equivalents of N,N-dimethylformamide, alkyl orthoforamtes or magnesium bromide formate.

Next, representative compounds of the present invention are given below but they are illustrated merely for better understanding of the present invention but the present invention is not deemed to be limited thereto.

1. 1,2-Dihydro-6-methyl-5-(2-methylimidazo[1,2-a]pyridin-6-yl)-2-oxo-3-pyridinecarbonitrile
2. 1,2-Dihydro-5-(imidazo[1,2-a]pyridin-6-yl)-6-methyl-2-oxo-3-pyridinecarbonitrile
3. 1,2-Dihydro-6-ethyl-5-(imidazo[1,2-a]pyridin-6-yl)-2-oxo-3-pyridinecarbonitrile
4. 1,2-Dihydro-6-ethyl-5-(2-methylimidazo[1,2-a]pyridin-6-yl)-2-oxo-3-pyridinecarbonitrile
5. 1,2-Dihydro-6-methyl-5-(2-methoxymethylimidazo[1,2-a]pyridin-6-yl)-2-oxo-3-pyridinecarbonitrile
6. 1,2-Dihydro-6-methyl-5-(7-methylimidazo[1,2-a]pyridin-6-yl)-2-oxo-3-pyridinecarbonitrile
7. 1,2-Dihydro-5-(7-methylimidazo[1,2-a]pyridin-6-yl)-2oxo-3-pyridinecarbonitrile
8. 5-(Imidazo[1,2-a]pyridin-6-yl)-2-methoxy-6-methyl-3-pyridinecarbonitrile
9. 5-(3-Bromoimidazo[1,2-a]pyridin-6-yl)-1,2-dihydro-6-methyl-2-oxo-3-pyridinecarbonitrile
10. 5-(3-Chloroimidazo[1,2-a]pyridin-6-yl)-1,2-dihydro-6-methyl-2-oxo-3-pyridinecarbonitrile
11. 1,2-Dihydro-6-methyl-5-(2-phenylimidazo[1,2-a]pyridin-6-yl)-2-oxo-3-pyridinecarbonitrile
12. 5-(3-Bromo-2-methylimidazo[1,2-a]pyridin-6-yl)-1,2-dihydro-6-methyl-2-oxo-3-pyridinecarbonitrile
13. 1,2-Dihydro-5-(imidazo[1,2-a]pyridin-6-yl)-6-methyl-2-oxo-3-pyridinecarboxamide
14. 1,2-Dihydro-5-(imidazo[1,2-a]pyridin-6-yl)-6-methyl-2-(1H)-pyridinone
15. 1,2-Dihydro-5-(5-fluoroimidazo[1,2-a]pyridin-6-yl)-6-methyl-2-oxo-3-pyridinecarbonitrile
16. 3-Amino-1,2-dihydro-5-(imidazo[1,2-a]pyridin-6-yl)-6-methyl-2(1H)-pyridinone
17. 1,2-Dihydro-5-(2-ethylimidazo[1,2-a]pyridin-6-yl)-6-methyl-2-oxo-3-pyridinecarbonitrile
18. 1,2-Dihydro-6-methyl-2-oxo-5-(2-n-propylimidazo[1,2-a]pyridin-6yl)-3-pyridinecarbonitrile
19. 5-(2-Chloroimidazo[1,2-a]pyridin-6-yl)-1,2-dihydro-6-methyl-2-oxo-3-pyridinecarbonitrile
20. 1,2-Dihydro-5-(imidazo[1,2-a]pyridin-6-yl)-2-oxo-3-pyridinecarbonitrile
21. 1,2-Dihydro-5-(5-methylimidazo[1,2-a]pyridin-6-yl)-2-oxo-3-pyridinecarbonitrile
22. 1,2-Dihydro-6-methyl-5-(5-methylimidazo[1,2-a]pyridin-6-yl)-2-oxo-3-pyridinecarbonitrile
23. 1,2-Dihydro-5-[2-(1H-imidazo[1,2-a]pyridin-1-yl)imidazo[1,2-a]pyridin-6-yl)-6-methyl-2-oxo-3-pyridinecarbonitrile
24. 1,2-Dihydro-5-(3-fluoroimidazo[1,2-a]pyridin-6-yl)-6-methyl-2-oxo-3-pyridinecarbonitrile
25. 1,2-Dihydro-5-(5-fluoro-2-methylimidazo[1,2-a]pyridin-6-yl)-6-methyl-2-oxo-3-pyridinecarbonitrile
26. 1,2-Dihydro-5-(2-ethyl-5-fluoroimidazo[1,2-a]pyridin-6-yl)-6-methyl-2-oxo-3-pyridinecarbonitrile
27. 1,2-Dihydro-5-(8-fluoroimidazo[1,2-a]pyridin-6-yl)-6-methyl-2-oxo-3-pyridinecarbontrile
28. 1,2-Dihydro-5-(imidazo[1,2-a]pyridin-6-yl)-4-methyl-2-oxo-3-pyridinecarbonitrile
29. 1,2-Dihydro-5-(7-methylimidazo[1,2-a]pyridin-6-yl)-2-oxo-3-pyridinecarbonitrile
30. 1,2-Dihydro-5-(2-dimethylaminomethylimidazo[1,2-a]pyridin-6-yl)-2-oxo-3-pyridinecarbonitrile Experiment 1

Effects of compounds on contractile response of isolated Guinea Pig heart muscles Male guinea pigs weighing 300 to 500 g were stunned with a flow on the head and exsanguinated. The chest was opened rapidly, the heart was excised and papillary muscles from the right ventricle were excised.

The preparations were mounted in 10 ml organ bath which were filled with Krebs-Henseleit solution maintained at 36° C. and oxzenated with 95% $O_2$–5% $CO_2$.

Right ventricular papillary muscles were stimulated electrically at a rate of 1 Hz by a suprathreshold (1.2×threshold) rectangular pulse 3 ms in duration. The resting tension applied to the papillary muscles was adjusted to produce maximum developed tension. The developed tension was recorded isometrically by means of force-displacement transducer. The test compounds were dissolved in diluted hydrochloric acid and were added to the bath. Contractility after administration was compared to that prior to administration.

The test compounds are those prepared in the examples later described.

The results are shown in Table 1.

TABLE 1

| Test Compound | Concentration (M) | Contractilities (%) |
|---|---|---|
| Example 1 | $10^{-6}$ | 40.7 |
|  | $10^{-5}$ | 88.0 |
|  | $10^{-4}$ | 128.8 |
| Example 2 | $10^{-6}$ | 34.1 |
|  | $10^{-5}$ | 73.5 |
|  | $10^{-4}$ | 106.4 |
| Example 7 | $10^{-6}$ | 56.7 |
|  | $10^{-5}$ | 95.7 |
|  | $10^{-4}$ | 129.7 |
| Example 10 | $10^{-6}$ | 37.9 |

TABLE 1-continued

| Test Compound | Concentration (M) | Contractilities (4%) |
|---|---|---|
| | $10^{-5}$ | 76.3 |
| | $10^{-4}$ | 110.1 |

Experiment 2
Effect of compounds on cardiac contractility in Anesthetized Dog

Using male and female mongrel dogs subjected to artificial respiration and anesthetized by inhalation of Halothane cardiotonic effect of compounds was examined. The aortic pressure and the left ventricular pressure were recorded with a catheter inserted from the femoral artery into the aorta of the chest and with a micro tip pressure transducer (Millar) inserted from the carotid into the left ventricle, respectively. The heart rate was monitored by means of a tachograph triggered by the left ventricular pressure pulse. As an index of cardiac contractility, a primary differentiation (LV dp/dt max) of the left ventricular pressure pulse was recorded. The test compounds were dissolved in physiological saline or diluted hydrochloric acid or polyethylene glycol and the solutions were intravenously given through the catheter inserted into the femoral vein.

Percent changes by the test compounds in cardiac contractility, heart rate and blood pressure obtained by the foregoing method are shown in Table 2, when compared to those prior to administration of the test compounds. In Table 2, the test compounds are those prepared in the examples later described.

TABLE 2

| Test Compound (Example Compound) | Dose (μg/kg) | Change in Cardiac Contractility (LV dp/dt max) (%) | Change in Heart Rate (%) | Change in Blood Pressure (%) |
|---|---|---|---|---|
| Example 1 | 10 | 16 | 6 | 0 |
| | 30 | 68 | 15 | −5 |
| | 100 | 97 | 22 | −17 |
| Example 6 | 10 | 14 | 0 | −1 |
| | 30 | 30 | 5 | −2 |
| | 100 | 58 | 10 | −7 |
| Example 7 | 10 | 21 | 8 | 0 |
| | 30 | 114 | 18 | −13 |
| Example 10 | 10 | 11 | 2 | −2 |
| | 30 | 25 | 4 | −5 |
| Example 14 | 300 | 10 | 6 | −6 |
| | 1000 | 41 | 0 | −4 |

Experiment 3
Effect of compounds on coronary and femoral blood flow

Using male and femal mongrel dogs thoracotomized at the left 4th intercostal space under artificial respiration and inhalation anesthesia with Halothane, effect of coronary and femoral blood flow was examined by intrarterial administration. By placing an electromagnetic flowprobe around the left circumflex coronary artery and the femoral artery, the blood flows of both arteries were measured. Shallow catheters were inserted in and fixed to the arterial branch distal to the flowprobe and the test compounds were intrarterially administered through the catheters. In this case, the blood pressure, the heart rate and the cardiac contractility were also recorded simultaneously. Each test compound was used by dissolving it in physiological saline, diluted hydrochloric acid or polyethylene glycol in a dose not accompanied by any change in the blood pressure, the heart rate and the cardiac contractility.

The results are shown in Table 3.

TABLE 3

| Compound of Example 1 dose (ug) | Coronary Blood Flow (Δ %) | Femoral Blood Flow (Δ %) |
|---|---|---|
| 3 | 25 | 18 |
| 10 | 63 | 51 |
| 30 | | 76 |

Experiment 4
Effect of compounds on platelet aggregation

Using platelets obtained from healthy volunteers, effect of compounds on platelet aggregation caused by collagen (1 μg/ml) was examined.

As a result, the compound of Example 1 showed inhibition rates of 14%, 41% and 90% at doses of $3 \times 10^{-7}$M, $1 \times 10^{-6}$M and $3 \times 10^{-6}$M, respectively.

From Experiments 1 to 4 above, it has made clear that the compounds of the present invention possess not only excellent cardiotonic effect, but also vasodilating effect and inhibitory effect of platelet aggregation.

Next, results of representative compounds of the present invention on acute toxicity test are shown below.

Test on Acute Toxicity

Acute toxicity was tested by oral administration in rats and mice. The results reveal that the compounds of the present invention have extremely low toxicity. More concretely, no death was noted with the compound of Example 1 by administration in a dose of 3 g/kg to all groups of the rats and mice (4 in each group).

Accordingly, the compounds of the present invention are characterized in that they possess excellent cardiotonic effect, extremely low toxicity and high safety. The extremely low toxicity is very important, taking into account that drugs for treating heart failures or cardiotonic agents must be continuously administered over long periods of time in nature and thus, the present invention is highly valuable.

Further in experiment where the compounds of the present invention were orally administered to conscious dogs, inclease of the cardiac contractility was noted without significantly affecting the heart rate and this effect was long-lasting. This long-lasting cardiotonic effect is also extremely important as drugs for treating heart failures or cardiotonic agents.

From the foregoing, it can be said that the compounds of the present invention are excellent drugs for treating heart failures having extremely high safety and long-lasting effect.

The compounds of the present invention are useful specifically for treatment of the following diseases.

That is, the compounds are useful as treating chronic congestive heart failures accompanied by old myocardial infraction, cardivalvulitis, dilated cardiomyopathy, hypertensive heart disease, etc.

When the compound of the present invention is administered to the patients with the above-mentioned diseases as agent for treating heart failure, its dose is not particularly limited because it varies depending upon kind of diseases, severity of disease, kind of compound, age of the patient, etc.; however, the compound is generally administered orally or perenterally to adult in a daily dose of about 10 mg to 1000 mg, preferably about 10 mg to 100 mg, once to 4 times a day.

Examples of preparation forms include powders, fine powders, granules, tablets, capsules, suppositories, injections, etc. In preparing the compounds into medical forms, they are prepared in a conventional manner using conventional carriers for medical preparations.

That is, in the case of preparing solid preparations for oral administration, a recipient and, if necessary, a binder, a disintegrader, a lubricant, a coloring agent, an agent for improving taste and odor, etc. are added to the active ingredient and then, the mixture is formed into tablets, coated tablets, granules, powders, capsules, etc. in a conventional manner.

Examples of the recipients include lactose, corn starch, refined sugar, glucose, sorbitol, crystalline cellulose silicon dioxide, etc. Examples of the binders include polyvinyl alcohol, polyvinyl ether, ethyl cellulose, methyl cellulose, gum arabic, tragacanth, gelatin, Shelac, hydroxypropylcellulose, hydroxypropyl starch, polyvinylpyrrolidone, etc. Examples of the disintegraders include starch, agar, gelatin powders, crystalline cellulose, calcium carbonate, hydrogen sodium carbonate, calcium citrate, dextrin, pectin, etc. Examples of the lubricants include magnesium stearate, talck, polyethylene glycol, silica, hardened vegetable oils, etc. Examples of the coloring agents include those that are permitted as additives to medical drugs. As the agents for improving taste and odor, there may be used cacao powders, menthol, aromatic acids, peppermint oil, borneol, cinnamon powders, etc. These tablets and granules may be appropriately coated by sugar coat, gelatin skin and other coat, if necessary.

In the case of preparing injections, the active ingredient is supplemented, if necessary, with a pH controlling agent, a buffer, a stabilizer, a solubilizing agent, etc. followed by forming into injections for subcutaneous, intramuscular or intravenous administration in a conventional manner.

Next, representative compounds of the present invention are given below but the present invention is not deemed to be limited thereto, needless to say.

EXAMPLE 1

1,2-Dihydro-5-(imidazo[1,2-a]pyridin-6-yl)-6-methyl-2-oxo-3-pyridinecarbonitrile In 230 ml of N,N-dimethylformamide was dissolved 23.5 g of 4-dimethylamino-3-(imidazo[1,2-a]pyridin-6-yl)-3-buten-2-one. The solution was stirred at 80° to 90° C. for 12 hours, together with 9.48 g of α-cyanoacetamide and 12.2 g of sodium methoxide. After cooling, the solvnt was removed by distillation under reduced pressure and 500 ml of water was added to the residue to dissolve it. The solution was washed with 600 ml of chloroform. Next, about 5 ml of acetic acid was added to the aqueous layer to adjust pH to 6.5. Crystals precipitated upon cooling were taken by filtration. After the crystals were washed with water, acetonitrile and then ether, they were dissolved in 200 ml of a 2.5% aqueous sodium hydroxide solution. The solution was treated with activated charcoal. The filtrate was again adjusted to pH of 6.5 with about 7 ml of acetic acid. Crystals precipitated upon cooling were taken by filtration. After the crystals were washed with water, acetonitrile and then ether, they were recrystallized from 100 ml of N,N-dimethylformamide to obtain 13 g of 1,2-dihydro-6-methyl-2-oxo-5-(imidazo[1,2-a]pyridin-6-yl)-3-pyridinecarbonitrile.

Melting point: >300° C.

Nuclear magnetic reasonoance spectrum (in DMSO-$d_6$)δ: 12.77 (b, s), 8.58 (1H, m), 8.15 (1H, s), 7.92 (1H, s), 7.61 (1H, s), 7.60 (1H, d, J=9 Hz). 7.22 (1H, dd, J=9, 2 Hz), 2.29 (3H, s).

EXAMPLES 2 THROUGH 8

Imidazo[1,2-a]pyridinylpyridone derivatives shown below were obtained in a manner similar to Example 1.

EXAMPLE 2

1,2-Dihydro-6-ethyl-5-(2-methylimidazo[1,2-a]pyridin-6-yl)-2-oxo-3-pyridinecarbonitrile Melting point: 274°–278° C. (decomposed).

Nuclear magnetic resonance spectrum (in DMSO-$d_6$): 12.68 (b, s), 8.44 (1H, m), 8.10 (1H, s), 7.65 (1H, s), 7.45 (1H, d, J=9 Hz), 7.08 (1H, dd, J=2, 9 Hz), 2.52 (2H, q, J=7 Hz), 2.33 (3H, s), 1.09 (3H, t, J=7 Hz).

EXAMPLE 3

1,2-Dihydro-6-methyl-5-(2-phenylimidazo[1,2-a]pyridin-6-yl)-3-pyridinecarbonitrile Melting point: >300° C. (decomposed).

Nuclear magnetic resonance spectrum (in DMSO-$d_6$): 12.80 (b, s), 8.55 (1H, s), 8.37 (1H, s), 8.17 (1H, s), 8.08~7.86 (2H, m), 7.62 (1H, d, J=10 Hz), 7.58~7.20 (3H, m), 7.23 (1H, dd, J=2, 10 Hz), 2.32 (3H, s).

EXAMPLE 4

1,2-Dihydro-5-(2-methoxymethylimidazo[1,2-a]pyridin-6-yl)-6-methyl-2-oxo-3-pyridinecarbonitrile Melting point: >270° C. (decomposed).

Nuclear magnetic resonance spectrum (in DMSO-$d_6$): 12.70 (b, s), 8.56 (1H, m), 8.14 (1H, s), 7.82 (1H, s), 7.52 (1H, d, J=9 Hz), 7.18 (1H, dd, J=2, 9 Hz), 4.49 (2H, s), 3.32 (3H, s), 2.28 (3H, s).

EXAMPLE 5

1,2-Dihydro-6-methyl-5-(7-methylimidazo[1,2-a]pyridin-6-yl)-2-oxo-3-pyridinecarbonitrile Melting point: >300° C. (decomposed).

Nuclear magnetic resonance spectrum (in DMSO-$d_6$): 12.74 (b, s), 8.36 (1H, s), 8.03 (1H, s), 7.80 (1H, s), 7.50 (1H, s), 7.44 (1H, s), 2.08 (6H, s).

EXAMPLE 6

1,2-Dihydro-6-ethyl-5-(2-methylimidazo[1,2-a]pyridin-6-yl)-2-oxo-3-pyridinecarbonitrile Melting point: 250°–252° C. (decomposed).

Nuclear magnetic resonance spectrum (in DMSO-$d_6$): 12.72 (b, s), 8.58 (1H, m), 8.12 (1H, s), 7.96 (1H, s), 7.64 (1H, s), 7.63 (1H, d, J=9 Hz), 7.20 (1H, dd, J=2, 9 Hz), 2.49 (2H, q, J=7 Hz), 1.10 (3H, t, J=7 Hz).

EXAMPLE 7

1,2-Dihydro-6-methyl-5-(2-methylimidazo[1,2-a]pyridin-6-yl)-2-oxo-3-pyridinecarbonitrile Melting point: >260° C. (decomposed).

Nuclear magnetic resonance spectrum (in DMSO-$d_6$): 12.80 (b, s), 8.50 (1H, m), 8.15 (1H, s), 7.68 (1H, s), 7.49 (1H, d, J=9 Hz), 7.17 (1H, dd, J=2, 9 Hz), 2.34 (3H, s), 2.28 (3H, s).

EXAMPLE 8

1,2-Dihydro-6-methyl-5-(5-methylimidazo[1,2-a]pyridin-6-yl)-2-oxo-3-pyridinecarbonitrile Melting point: >330° C. (decomposed).

Nuclear magnetic resonance spectrum (in DMS0-d$_6$): 12.68 (1H, b, s), 8.02 (1H, s), 7.88 (1H, d, J=1 Hz), 7.66 (1H, d, J=1 Hz), 7.50 (1H, d, J=10 Hz), 7.08 (1H, d, J=10 Hz), 2.42 (3H, s), 2.10 (3H, s).

EXAMPLE 9

1,2-Dihydro-6-methyl-5-(imidazo[1,2-a]pyridin-6-yl)-2-oxo-3-pyridinecarbonitrile In 15 ml of conc. sulfuric acid, 3 g of 1,2-dihydro-6-methyl-5-(imidazo[1,2-a]pyridin-6-yl)-2-oxo-3-pyridinecarbonitrile was stirred at 90° C. for 40 minutes. After cooling, the reaction mixture was poured into ice and conc. ammonia water was added thereto to render alkaline. Crystals prepcipitated were taken by filtration. After washing with water and drying, the crystals were recrystallized from N,N-dimethylformamide to obtain 2.5 g of 1,2-dihydro-6-methyl-5-(imidazo[1,2-a]pyridin-6-yl)-2-oxo-3-pyridinecarbonitrile.

Melting point: >300° C.

Nuclear magnetic reasonance spectrum (in DMSO-d$_6$): 12.58 (b, s), 9.0 (b, d, 1H), 8.6 (b, d, J=1 Hz), 8.2 (1H, s), 7.92 (1H, s), 7.7~7.4 (3H, b, s), 7.22 (1H, dd, J=2, 10 Hz), 2.32 (3H, s).

EXAMPLE 10

1,2-Dihydro-6-methyl-5-imidazo[1,2-a]pyridin-6-yl)-2-oxopyridine

In 10 ml of 85% phosphoric acid was refluxed 1 g of 1,2-dihydro-6-methyl-5-(imidazo[1,2-a]pyridin-6-yl)-2-oxo-3-pyridinecarbonitrile for 18 hours. After cooling, water was added and then conc. ammonia water was further added to the reaction mixture to render alkaline. The mixture was extracted with chloroform. After washing with water and drying over magnesium sulfate, chloroform was removed by distillation under reduced pressure. The residue was recrystallized from ethanol-ether to obtain 0.4 g of 1,2-dihydro-6-methyl-5-(imidazo[1,2-a]pyridin-6-yl)-2-oxo-pyridine.

Melting point: 290°-292° C.

Nuclear magnetic resonance spectrum (in DMSO-d$_6$): 12.62(1H, b, s), 8.0(1H, d, J=1 Hz), 7.52~7.70 (3H, t-like), 7.4(1H, d, J=9.2 Hz), 7.06(1H, dd, J=2, 10 Hz), 6.52(1H, d, J=9.2 Hz), 2.38(3H, s).

EXAMPLE 11

5-(3-Bromoimidazo[1,2-a]pyridin-6-yl)-1,2-dihydro-6-methyl-2-oxo-3-pyridinecarbonitrile hydrobromide In 10 ml of acetic acid was dissolved 0.3 g of 1,2-dihydro-5-(imidazo[1,2-a]pyridin-6-yl)-6-methyl-2-oxo-3-pyridinecarbonitrile. To the solution 0.2 g of bromine was added and the mixture was warmed to 30° C. After cooling, precipitated white crystals were taken by filtration. After washing with ether, the crystals were recrystallized from methanol to obtain 0.4 g of 5-(3-bromoimidazo[1,2-a]pyridin-6-yl)-1,2-dihydro-6-methyl-2-oxo-3-pyridinecarbonitrile hydrobromide.

Melting point: >300° C.

Nuclear magnetic resonance spectrum (in DMSO-d$_6$): 12.90(b, s), 8.68(1H, s), 8.32(1H, s), 8.24(1H, s), 7.99(1H, d, J=9 Hz), 7.81(1H, dd, J=2, 9 Hz), 2.30(3H, s).

EXAMPLE 12

5-(3-Bromo-2-methylimidazo[1,2-a]pyridin-6-yl)-1,2-dihydro-6-methyl-2-oxo-3-pyridinecarbonitrile hydrobromide 1,2-Dihydro-5-(2-methylimidazo[1,2-a]pyridin-6-yl)-1,2-dihydro-6-methyl-2-oxo-3-pyridinecarbonitrile was treated in a manner similar to Example 11 to obtain 5-(3-bromo-2-methylimidazo[1,2-a]pyridin-6-yl)-1,2-dihydro-6-methyl-2-oxo-3-pyridinecarbonitrile hydrobromide.

Melting point: >300° C. (decomposed).

Nuclear magnetic resonance spectrum (in DMSO-d$_6$): 12.85(b, s), 8.65(1H, d J=2 Hz), 8.24(1H, s), 7.97(1H, d J=9 Hz), 7.82(1H, dd, J=2, 9 Hz), 2.48(3H, s), 2.28(3H, s).

EXAMPLE 13

5-(3-Chloroimidazo[1,2-a]pyridin-6-yl)-1,2-dihydro-6-methyl-2-oxo-3-pyridinecarbonitrile In 10 ml of N,N-dimethylformamide, 0.3 g of 1,2-dihydro-5-(imidazo[1,2-a]pyridin-6-yl)-6-methyl-2-oxo-3-pyridinecarbonitrile was stirred together with 0.19 g of N-chlorosuccinimide at 60° to 80° C. for 2 hours. After cooling, the solvent was removed by distillation under reduced pressure and water was added to the residue to take the solid by filtration. The solid was recrystallized from large quantities of methanol to obtain 0.1 g of 5-(3-chloroimidazo[1,2-a]pyridin-6-yl)-1,2-dihydro-6-methyl-2-oxo-3-pyridinecarbonitrile.

Melting point: >300° C.

Nuclear magnetic resonance spectrum (in DMSO-d$_6$): 12.82(b, s), 8.42(1H, s), 8.22(1H, s), 7.77(1H, s), 7.72(1H, d, J=9 Hz), 7.37(1H, dd, J=2, 9 Hz), 2.28(3H, s).

EXAMPLE 14

5-(Imidazo[1,2-a]pyridin-6-yl)-2-methoxy-6-methyl-2-oxo-3-pyridinecarbonitrile

A mixture of 3.1 g of 1,2-dihydro-5-(imidazo[1,2-a]pyridin-6-yl)-6-methyl-2-oxo-3-pyridinecarbonitrile, 30 ml of phosphorous oxychloride and 5 drops of dimethylformamide was stirred under reflux for 2 hours. An excess of phosphorous oxychloride was removed by distillation under reduced pressure and upon cooling, chloroform, a 20% NaOH solution and then an aqueous sodium carbonate solution were added to the residue to render alkaline. The organic layer was taken by fractionation. After the chloroform layer was dried over magnesium sulfate, chloroform was removed by distillation. The residue was purified by column chromatography to obtain 1.9 g of 2-chloro-5-(imidazo[1,2-a]pyridin-6-yl)-6-methyl-3-pyridinecarbonitrile.

Melting point: 185°-186° C.

Nuclear magnetic reasonance spectrum (in DMSO-d$_6$): 8.16(1H, m), 7.86(1H, s), 7.74(1H, d, J=10 Hz), 7.72(1H, s), 7.68(1H, s), 7.08(1H, dd J=2, 10 Hz), 2.6(3H, s).

In a solvent mixture of 30 ml of methylene chloride and 30 ml of methanol, 0.59 g of 2-chloro-5-(imidazo[1,2-a]pyridin-6-yl)-6-methyl-3-pyridinecarbonitrile described above was stirred under reflux for 3 hours. After cooling, the solvent was removed by distillation and chloroform-water was added to the residue. The chloroform was taken by fractionation. After washing with water and drying over magnesium sulfate, chloroform was removed by distillation under reduced pressure. The residue was recrystallized from benzene-n-hexane to obtain 0.75 g of 5-(imidazo[1,2-a]pyridin-6-yl)-2-methoxy-6-methyl-3-pyridinecarbonitrile.

Melting point: 195°–196° C.

Nuclear magnetic resonance spectrum (in CDCl$_3$): 8.04(1H, m), 7.74(1H, s), 7.7(1H, s), 7.68(1H, d, J=10 Hz), 7.62(1H, s), 7.06(1H, dd, J=2, 10 Hz), 4.07(3H, s), 2.46(3H, s).

Next, the starting materials and the intermediates used in Examples 1 through 8 are described in Examples 15 to 19.

EXAMPLE 15

1-(Imidazo[1,2-a]pyridin-6-yl)-2-propanone (1) To a 24.5 g of magnesium charged in a 4-necked flask of a 2 liter volume, a solution of 8.25 g of ethyl bromide in 14 ml of tetrahydrofuran was dropwise added under nitrogen flow. After completion of the dropwise addition, a solution of 49.25 g of 6-bromoimidazo[1,2-a]pyridine and 74.25 g of ethyl bromide in 300 ml of tetrahydrofuran was dropwise added to the mixture over 40 minutes while maintaining the internal temperature at 50° to 60° C. After completion of the dropwise addition, the reaction mixture was stirred under reflux for 1 hour to complete the formation of the Grignard reagent.

Next, the reaction mixture was cooled and a solution of 97.5 g of 2-chloromethyl-1-propene in 200 ml of tetrahydrofuran was dropwise added with stirring at the internal temperature of 0° to 10° C. After the dropwise addition, the mixture was stirred under reflux for 2 hours. After cooling (30° to 40° C.), a solution of 50 g of ammonium chloride in 500 ml of water was dropwise added to the reaction mixture. After cooling, 250 ml of toluene, 200 ml of n-hexane and 200 ml of water were added to the mixture. The organic layer was taken by fractionation. The organic layer was washed twice with a saturated saline solution and dried over magnesium sulfate. The solvent was removed by distillation under reduced pressure to obtain 30.5 g (70.9%) of 6-(2-methyl-2-propenyl)imidazo[1,2-a]pyridine.

Boiling point: 118°–122° C. (0.5 mm Hg).

Nuclear magnetic resonance spectrum (in CDCl$_3$): 7.94(1H, m), 7.72(1H, d J=1 Hz), 7.56(1H, d, J=9 Hz), 7.52(1H, d, J=1 Hz), 7.02(1H, dd, J=2, 9 Hz), 4.90(1H, d, J=1 Hz), 4.80(1H, d, J=1 Hz), 3.28(2H, s), 1.70(3H, s).

(2) In a solution of 12.3 g of conc. hydrochloric acid, 45 ml of water and 45 ml of methanol was dissolved 20 g of 6-isobutenylimidazo[1,2-a]pyridine. The solution was cooled to −5° C. Ozone was introduced to the solution at −5 to 0° C. for 4 hours. The endpoint of the reaction was confirmed by thin layer chromatography. After completion of the reaction, a solution of 30.6 g of sodium sulfite in 160 ml of water was dropwise added under cooling at such a rate that the temperature did not exceed 20° C. Next, 22 g of sodium bicarbonate and an appropriate amount of salt were added as solids and the mixture was extracted with chloroform. The chloroform extract was washed twice with a saturated saline solution. After drying over magnesium sulfate, chloroform was removed by distillation under reduced pressure. The residue was purified by distillation under reduced pressure to obtain 14.2 g (70.5%) of 1-(imidazo[1,2-a]pyridin-6-yl)-2-propanone.

Boiling point: 155°–159° C. (0.4 mm Hg).

Nuclear magnetic resonance spectrum (in CDCl$_3$): 8.03(1H, m), 7.64(1H, s), 7.60(1H, d, J=9 Hz), 7.56(1H, s), 6.95(1H, dd, J=2, 9 Hz), 3.70(2H, s), 2.24(3H, s).

EXAMPLE 16

1-(Imidazo[1,2-a]pyridin-6-yl)-2-propanone:

(1) In 40 ml of ethanol, 6.9 g of 6-imidazo[1,2-a]pyridinecarbaldehyde was stirred under reflux for 14 hours, together with 10.6 g of nitroethane and 30 drops of n-butyl amine. Then, a small quantity of ethyl amine was added thereto and the mixture was stirred under reflux for further 18 hours. After insoluble matters were removed by filtration upon heating, 50 ml of ethanol and 150 ml of ether were further added to remove insoluble matters by filtration. The solvent was removed by distillation under reduced pressure and the residue was recrystallized twice from ethanol to obtain 1.14 g of 6-(2-nitro-1-propenyl)imidazo[1,2-a]pyridine.

Melting point: 190°–192° C. (decomposed).

Nuclear magnetic resonance spectrum (in CDCl$_3$): 8.30(1H, d, J=2 Hz), 8.04(1H, d, J=1 Hz), 7.73(1H, d, J=1 Hz), 7.70(1H, d, J=9 Hz), 7.66(1H, d, J=1 Hz), 7.26(1H, dd, J=2, 9 Hz), 2.52(3H, d, J=1 Hz).

(2) In 25 ml of water and 25 ml of EtOH, 1.14 g of 6-(2-nitro-1-propenyl)imidazo[1,2-a]pyridine was heated to 80° C. together with 100 mg of ferrous chloride. With stirring, 2.5 ml of conc. hydrochloric acid was added at a refluxing rate and the mixture was stirred for 1 hour. Upon heating, insoluble matters were removed by filtration. After the insoluble matters were thoroughly washed with ethanol, the solvent was removed by distillation under reduced pressure. An aqueous sodium bicarbonate solution was added to the residue and the mixture was extracted with chloroform. After washing with water and drying over magnesium sulfate, chloroform was removed by distillation under reduced pressure. The residue was purified by column chromatography to obtain 500 mg of 1-(imidazo[1,2-a]pyridin-6-yl)-2-propanone.

The nuclear magnetic resonance spectrum was identical with that obtained in Example 15.

EXAMPLE 17

The reaction was conducted in a manner similar to Example 15 except that 6-bromo-2-methylimidazo[1,2-a]pyridine, 6-bromo-2-phenylimidazo[1,2-a]pyridine, 6-bromo-2-methoxymethylimidazo[1,2-a]pyridine, 6-bromo-7-methylimidazo[1,2-a]pyridine or 6-bromo-5-methylimidazo[1,2-a]pyridine was used instead of 6-bromoimidazo[1,2-a]pyridine in Example 15 and instead of 2-chloromethyl-1-propene, 2-chloromethyl-1-butene was used. The corresponding propene, butene, propane and butanone derivatives shown below were obtained, respectively. Hereafter, the compounds obtained and their nuclear magnetic resonance spectra are shown, wherein Compounds ① to ⑦ described below correspond to (1) in Example ⑮ and Compounds ⑧ to ⑭ correspond to (2) in Example 15.

① 2-Methyl-6-(2-methyl-2-propenyl)imidazo[1,2-a]pyridine

Nuclear magnetic resonance spectrum (in CDCl$_3$): 7.84(1H, m), 7.44(1H, d, J=9 Hz), 7.28(1H, s), 6.97(1H, dd, J=2, 9 Hz), 4.87(1H, s), 4.78(1H, s), 3.25(2H, s), 2.44(3H, s), 1.70(3H, s).

② 6-(2-Methyl-2-propenyl)-2-phenylimidazo[1,2-a]pyridine

Melting point: 122°–125° C.

Nuclear magnetic resonance spectrum (in CDCl₃): 7.96(1H, d, J=2 Hz), 7.98~7.78(2H, m), 7.77(1H, s), 7.53(1H, d, J=9 Hz), 7.52~7.20(3H, m), 7.01(1H, dd, J=2, 7 Hz), 4.87(1H, s), 4.78(1H, s), 3.27(2H, s), 1.70(3H, s).

③ 2-Methoxymethyl-6-(2-methyl-2-propenyl)imidazo[1,2-a]pyridine:

Nuclear magnetic resonance spectrum (in CDCl₃): 7.86(1H, m), 7.48(1H, s), 7.46(1H, d, J=9 Hz), 6.99(1H, dd, J=2, 9 Hz), 4.86(1H, s), 4.76(1H, s), 4.61(2H, s), 3.48(3H, s), 3.26(2H, s), 1.70(3H, s).

④ 7-Methyl-6-(2-methyl-2-propenyl)imidazo[1,2-a]pyridine:

Nuclear magnetic resonance spectrum (in CDCl₃): 7.82(1H, s), 7.50(1H, s), 7.42(1H, s), 7.34(1H, s), 4.85(1H, s), 4.54(1H, s), 3.20(2H, s), 2.28(3H, s), 1.76(3H, s).

④ 6-(2-Ethyl-2-propenyl)imidazo[1,2-a]pyridine:

Nuclear magnetic resonance spectrum (in CDCl₃): 7.90(1H, m), 7.56(1H, s), 7.52(1H, d, J=9 Hz), 7.50(1H, s), 6.98(1H, dd, J=2, 9 Hz), 4.88(1H, d, J=1 Hz), 4.76(1H, d, J=1 Hz), 3.29(2H, s), 2.00 (2H, q, J=7 Hz), 1.04(3H, t, J=7 Hz).

⑥ 6-(2-Ethyl-2-propenyl)-2-methylimidazo[1,2-a]pyridine:

Nuclear magnetic resonance spectrum (in CDCl₃): 7.80(1H, m), 7.39(1H, d, J=9 Hz), 7.24(1H, s), 6.92(1H, dd, J=2, 9 Hz), 4.86(1H, s), 4.74(1H, s), 3.25(2H, s), 2.38(3H, s), 1.99(2H, q, J=7 Hz), 1.02(3H, t, J=7 Hz).

⑦ 5-Methyl-6-(2-methyl-2-propenyl)imidazo[1,2-a]pyridine:

Nuclear magnetic resonance spectrum (in CDCl₃): 7.66(1H, d, J=2 Hz), 7.50(1H, d, J=10 Hz), 7.46(1H, d, J=2 Hz), 7.02(1H, d, J=2 Hz), 4.82(1H, s), 4.56(1H, s), 3.34(2H, s), 2.50(3H, s), 1.74(3H, s).

⑧ 1-(2-Methylimidazo[1,2-a]pyridin-6-yl)-2-propanone:

Nuclear magnetic resonance spectrum (in CDCl₃): 7.93(1H, m), 7.47(1H, d, J=9 Hz), 7.30(1H, s), 6.94(1H, dd, J=2, 9 Hz), 3.66(2H, s), 2.44(3H, s), 2.22(3H, s).

⑨ 1-(2-Phenylimidazo[1,2-a]pyridin-2-yl)-2-propanone:

Melting point: 144°–147° C.

Nuclear magnetic resonance spectrum (in CDCl₃): 8.10~7.82(4H, m), 7.80(1H, s), 7.58(1H, d, J=10 Hz), 7.55~7.24(3H, m), 6.96(1H, dd, J=2, 10 Hz), 3.68(1H, s), 2.24(3H, s).

⑩ 1-(2-Methoxymethylimidazo[1,2-a]pyridin-2-yl)-2-propanone:

Nuclear magnetic resonance spectrum (in CDCl₃): 7.90(1H, m), 7.50(1H, s), 7.48(d, J=9 Hz), 6.94 (1H, dd, J=2, 9 Hz), 4.60(2H, s), 3.68(2H, s), 3.48(3H, s), 2.24(3H, s).

⑪ 1-(7-Methylimidazo[1,2-a]pyridin-2-yl)-2-propanone:

Melting point: 123°–125° C.

Nuclear magnetic resonance spectrum (in CDCl₃): 7.90(1H, s), 7.53(1H, s), 7.45(1H, s), 7.38(1H, s), 3.68(2H, s), 2.24(6H, s).

⑫ 1-(Imidazo[1,2-a]pyridin-2-yl)-2-butanone:

Nuclear magnetic resonance spectrum (in CDCl₃): 7.98(1H, d, J=2 Hz), 7.56(1H, s), 7.53(1H, d, J=9 Hz), 7.50(1H, s), 6.94(1H, dd, J=2, 9 Hz), 3.64(2H, s), 2.52(2H, q, J=7 Hz), 1.06(3H, t, J=7 Hz).

⑬ 1-(2-Methylimidazo[1,2-a]pyridin-2-yl)-2-butanone:

Nuclear magnetic resonance spectrum (in CDCl₃): 7.76(1H, m), 7.30(1H, d, J=9 Hz), 7.12(1H, s), 6.76(1H, dd, J=2, 9 Hz). 3.48(2H, s), 2.40(2H, q, J=7 Hz), 2.30(3H, s), 0.94(3H, t, J=7 Hz).

⑭ 1-(5-Methylimidazo[1,2-a]pyridin-2-yl)-2-propanone:

Melting point: 70°–73° C.

Nuclear magnetic resonance spectrum (in CDCl₃): 7.61(1H, d, J=1 Hz), 7.46(1H, d, J=10 Hz), 7.42(1H, d, J=1 Hz), 6.92(1H, d, J=10 Hz), 3.92(1H, d, J=10 Hz), 3.71(2H, s), 2.44(3H, s), 2.12(2H, s).

EXAMPLE 18

4-Dimethylamino-3-(imidazo[1,2-a]pyridin-6-yl)-3-buten-2-one

In 200 ml of N,N-dimethylformamide, 33.17 g of 1-(imidazo[1,2-a]pyridin-6-yl)-2-propanone was stirred at 80° C. for 1 hour, together with 45.4 g of N,N-dimethylformamide dimethyl acetal. After cooling, the solvent was removed by distillation under reduced pressure. The residue was purified by silica gel chromatography (eluted with chloroform-methanol=97:3) to obtain 32.46 g (74.5%) of 4-dimethylamino-3-(imidazo[1,2-a]pyridin-6-yl)-3-buten-2-one.

Nuclear magnetic resonance spectrum (in CDCl₃): 7.94(1H, m), 7.63(2H, s), 7.57(1H, d, J=9 Hz), 7.55(1H, s), 7.02(1H, dd, J=2.9 Hz), 2.80(6H, s), 2.04(3H, s).

EXAMPLE 19

Dimethylaminoethenyl derivatives ① to ⑦ described below were prepared in a manner similar to Example 18.

① 4-Dimethylamino-3-(2-methylimidazo[1,2-a]pyridin-6-yl)-3-buten-2-one:

Nuclear magnetic resonance spectrum (in CDCl₃): 7.87(1H, d, J=2 Hz), 7.66(1H, s), 7.48(1H, d, J=9 Hz), 7.32(1H, s), 6.98(1H, dd, J=2, 9 Hz), 2.78(6H, s), 2.46(3H, s), 2.02(3H, s).

② 4-Dimethylamino-3-(2-phenylimidazo[1,2-a]pyridin-6-yl)-3-buten-2-one:

Melting point: higher than 253° C. (decomposed).

Nuclear magnetic resonance spectrum (in CDCl₃): 8.28(1H, s), 8.18(1H, s), 8.01~7.78(2H, m), 7.76(1H, s), 7.55~7.20(4H, m), 6.97(1H, dd, J=1, 9 Hz), 2.76(6H, s), 2.05(3H, s).

③ 4-dimethylamino-3-(7-methylimidazo[1,2-a]pyridin-6-yl)-3-buten-2-one:

Melting point: 193°–198° C. (decomposed).

Nuclear magnetic resonance spectrum (in CDCl₃): 7.88(1H, s), 7.66(1H, s), 7.53(1H, d, J=1 Hz), 7.45(1H, d, J=1 Hz), 7.41(1H, s), 2.76(6H, s), 2.21(3H, s), 1.96(3H, s).

④ 4-Dimethylamino-3-(2-methoxymethylimidazo[1,2-a]pyridin-6-yl)-3-buten-2-one:

Melting point: 163°–165° C.

Nuclear magnetic resonance spectrum (in CDCl₃): 7.86(1H, d, J=2 Hz), 7.60(1H, s), 7.50(1H, s), 7.46(1H, d, J=10 Hz), 6.98(1H, dd, J=2, 10 Hz), 4.6(2H, s), 3.48(3H, s), 2.78(6H, s), 2.0(3H, s).

⑤ 1-Dimethylamino-2-(imidazo[1,2-a]pyridin-6-yl)-1-penten-3-one:

Nuclear magnetic resonance spectrum (in CDCl₃): 7.92(1H, d, J=2 Hz), 7.64(1H, s), 7.62(1H, d, J=1 Hz), 7.60(1H, d, J=9 Hz), 7.52(1H, d, J=1 Hz), 7.00(1H, dd, J=2, 9 Hz), 2.77(6H, s), 2.28(2H, q, J=7 Hz), 1.01(3H, t, J=7 Hz).

⑥ 1-Dimethylamino-2-(2-methylimidazo[1,2-a]pyridin-6-yl)-2-penten-3-one:

Nuclear magnetic resonance spectrum (in CDCl₃):
7.80(1H, d, J=2 Hz), 7.56(1H, s), 7.36(1H, d, J=9 Hz), 7.24(1H, s), 6.90(1H, dd, J=2, 9 Hz), 2.70(6H, s), 2.36(3H, s), 2.21(2H, g, J=7 Hz), 0.92(3H, t, J=7 Hz).

⑦ 1-Dimethylamino-2-(5-methylimidazo[1,2-a]pyridin-6-yl)-2-penten-3-one:

Nuclear magnetic resonance spectrum (in CDCl₃):
7.68(2H, s), 7.52(1H, d, J=10 Hz), 7.47(1H, s), 7.04(1H, d, J=10 Hz), 2.74(6H, s), 2.48(3H, s), 1.95(3H, s).

While the invention has been described in detail and with reference to specific embodiments thereof, it will be apparent to one skilled in the art that various changes and modifications can be made therein without departing from the spirit and scope thereof.

What is claimed is:

1. A compound represented by the formula:

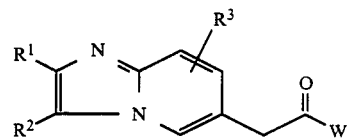

$R^1$ represents a hydrogen atom, a lower alkyl group, phenyl group or a group shown by formula: —$CH_2R^4$ in which $R^4$ is a lower alkoxy group or a group shown by formula:

in which $R^5$ and $R^6$ are hydrogen atom or a lower alkyl group; $R^2$ represents hydrogen atom or a halogen atom; and $R^3$ represents hydrogen atom, a lower alkyl group or a halogen atom; and W represents hydrogen or a lower alkyl group.

* * * * *